United States Patent [19]

Kring

[11] 4,269,804
[45] * May 26, 1981

[54] SELF-CONTAINED GASEOUS CONTAMINANT DOSIMETER

[75] Inventor: Elbert V. Kring, Wilmington, Del.

[73] Assignee: E. I. Du Pont de Nemours and Company, Wilmington, Del.

[*] Notice: The portion of the term of this patent subsequent to Jun. 17, 1997, has been disclaimed.

[21] Appl. No.: 99,704

[22] Filed: Dec. 3, 1979

Related U.S. Application Data

[63] Continuation-in-part of Ser. No. 69,574, Aug. 24, 1979, abandoned, which is a continuation-in-part of Ser. No. 922,546, Jul. 7, 1978, Pat. No. 4,208,371.

[51] Int. Cl.³ .................... B01D 53/22; B01D 59/10; G01N 31/22; G01N 33/00
[52] U.S. Cl. .................... 422/86; 23/232 R; 55/158; 73/23; 422/61; 422/88; 116/206
[58] Field of Search .................... 422/61, 83–88, 422/119; 23/232 R; 73/23, 421.5; 116/206; 55/16, 158

[56] References Cited

U.S. PATENT DOCUMENTS

| 3,113,842 | 12/1963 | Udall | 422/86 |
| 3,476,515 | 11/1969 | Johnson et al. | 422/61 X |
| 3,726,645 | 4/1973 | Kaczmarek | 422/61 |
| 3,740,196 | 6/1973 | Stroterhoff | 422/61 |
| 3,992,153 | 11/1976 | Ferber | 23/232 R |
| 4,137,049 | 1/1979 | Couch | 116/206 |

Primary Examiner—Michael S. Marcus

[57] ABSTRACT

A personal dosimeter for measuring the average concentration of a gaseous contaminant over a given period of time is provided. The dosimeter comprises a sealed pouch having a reaction chamber, which contains a gas-collecting medium, and at least one compartment. Each compartment can be separately sealed and can contain a different reagent, the seals being individually breakable such that the reagents can be separately released into the reaction chamber. Into the pouch is sealed a gas diffusion device that permits the contaminant to diffuse into the reaction chamber where it is collected in proportion to its ambient concentration.

11 Claims, 4 Drawing Figures

SELF-CONTAINED GASEOUS CONTAMINANT DOSIMETER

CROSS REFERENCE TO RELATED APPLICATIONS

This application is a continuation-in-part of co-pending application Ser. No. 069,574, filed Aug. 24, 1979, abandoned, which is a continuation-in-part of copending Ser. No. 922,546, filed July 7, 1978 now U.S. Pat. No. 4,208,371.

BACKGROUND OF THE INVENTION

1. Field of the Invention

This invention is related to a personal dosimeter for registering gaseous contaminants in the atmosphere. More particularly it is related to a self-contained dosimeter capable of integrating the exposure level of a gaseous contaminant over a given period of time.

2. Description Of The Prior Art

In response to the increasing concern about the health of workers who are exposed to harmful pollutants in the air, it has become necessary to monitor the concentration of the air-borne contaminants. One development for this purpose involved a rather large air pump which would force air to be sampled through a filter, trapping particulate contaminants. This obviously is unavailing for the monitoring of gas contaminants and, even for particles, is not accurate to determine concentration of the particles in the sampled atmosphere.

Personal sampling devices which are worn by individual workers and which passively collect the contaminants have also been used. For example, a device which utilizes the molecular diffusion of the gas to be monitored to collect the sample has been described in American Industrial Hygiene Association Journal, Volume 34, pages 78-81 (1973). This device, however, requires that the collecting medium be removed therefrom, and carefully treated with reagents which must be exactly-measured at each analysis.

The disassembly of the device and use of cumbersome reagents required for each analysis are disadvantageous.

Therefore, there remains a need for a personal dosimeter for gaseous contaminants which accurately integrates, that is, indicates the average concentration of the gaseous contaminant over a given time period, and which easily lends itself to analysis without removal of the gas-collecting medium or bothersome addition of other elements.

SUMMARY OF THE INVENTION

According to the present invention, there is provided a personal dosimeter for measuring the average concentration of a gaseous contaminant over a given period of time comprising: a sealed pouch-like receptacle of a pliable polymeric material, said receptacle having a reaction chamber adapted to contain a gas-collecting medium and at least one compartment separately sealed and adapted to contain a testing reagent, the seals of each compartment being individually breakable such that the reagents can be separately released into the reaction chamber; and a gas diffusion device which is sealed into a boundary of the receptacle, the diffusion device providing the only communication between the atmosphere and the interior of the reaction chamber.

DETAILED DESCRIPTION OF THE INVENTION

The dosimeters of this invention collect a gaseous contaminant in proportion to its average concentration in the atmosphere during the collection period and provide for the expedient determination of this concentration. This is achieved by passively sampling the gaseous contaminant in ambient air in proportion to its concentration therein by allowing the contaminant to diffuse into an interior portion of the dosimeter where it is maintained until it is analyzed. The dosimeter further contains specified color-forming reagents, separately sealed in measured amounts within the dosimeter but capable of being brought into contact with the collecting medium.

The collecting medium, which is present in a measured amount, holds the gaseous contaminant or its ions in a form that is more readily analyzable than is the gaseous form. After collection, the medium is treated with the appropriate reagents to product color, the intensity of which is dependent upon the amount of gaseous contaminant collected. The time-average ambient concentration can then be determined, as later explained, with a previously-calibrated colorimeter or spectrophotometer.

Generally, the collecting medium is a material that absorbs, adsorbs, reacts or otherwise combines with the gaseous contaminant being measured. Regardless of the manner in which the medium interacts, as above, with the contaminant, the quantity or strength of the collecting medium in the dosimeter should be sufficient to interact completely with the total quantity of gaseous contaminant which is anticipated to be collected. The collecting medium will often be specific to the particular gaseous contaminant being monitored. Examples, meant to be representative but not limiting, include aqueous solutions of oxidizing agents or triethanol amine to absorb nitrogen dioxide, solutions of potassium or sodium tetrachloromercurate to absorb sulfur dioxide, and solutions of sulfuric or other acids to absorb ammonia. Charcoal or powdered carbon of high surface-area, powders of metals or metal salts, or films can be used to adsorb may organic contaminants.

Methods for colorimetric analysis, for example, for sulfur dioxide, nitrogen dioxide, and ammonia, in air, are described in National Institute for Occupational Safety and Health method numbers 160(publication 121, 1975), 108 (publication 136, 1974), and 205(publication 121, 1975), respectively. The techniques therein described are readily adaptable with respect to absorbing solution and color-forming reagents for use in the dosimeter of the present invention.

Figure 1:
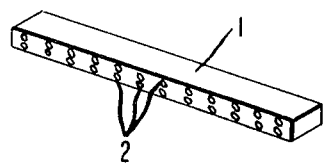
FIG. 1 is a magnified perspective view of a gas diffusion device usable in the present invention.
Figure 2:
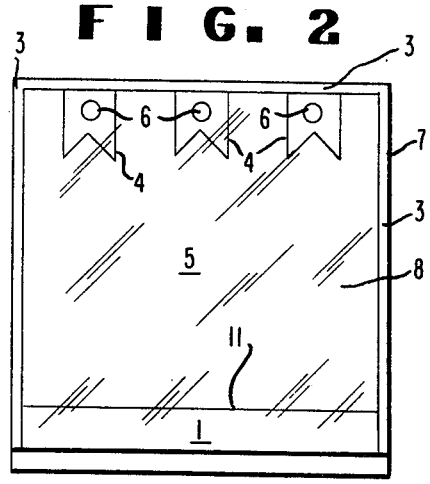
FIG. 2 is a top view of a gaseous contaminant dosimeter utilizing the diffusion device of FIG. 1.
Figure 3:
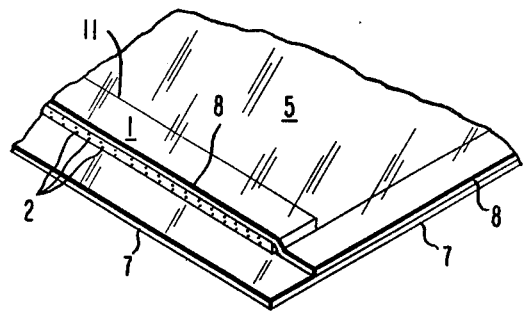
FIG. 3 is a partial perspective view of the dosimeter of FIG. 2.

One embodiment of the present invention is shown in FIGS. 2 and 3 and is described and can be formed as follows. A base sheet 7 of impermeable polymeric material, which is preferably pliable, is provided with at least one depression 6. Normally, there will be several depressions 6 which can be linearly spaced along a periphery of the sheet 7 as shown. The sheet is preferably transparent and thermoplastic and can be made of polymers of olefin, halogenated polymers, polyester, or ionomer resins. Preferred materials are shown in U.S. Pat. No. 3,264,272 issued Aug. 2, 1966 to R. W. Rees. They are the ionic copolymers of alpha-olefins and alpha, beta-ethylenically unsaturated carboxylic acids of 3-8 carbon atoms having 10-90% of the carboxylic acid groups neutralized with metal ions.

The size of sheet 7 is not critical but is preferably a size easily adaptable for use in a personal dosimeter which is to be worn or readily carried. The depressions 6 can easily be formed by applying pressure to sheet 7 with an appropriate die, heated or otherwise.

Pre-measured amounts of reagents are placed in any convenient manner in the depressions 6. The collecting medium is placed in the central portion of sheet 7. When the collecting medium is a liquid, this can be more easily accomplished by first forming a depression in the central portion of the sheet in a manner similar to that used in the formation of depressions 6. This central depression is normally larger than any of depressions 6.

After the reagents and collecting medium have been placed on sheet 7, a second, top sheet 8 corresponding to sheet 7 in composition and substantially in size is placed over sheet 7. Heat and pressure are then applied to the areas 4 surrounding the reagent-containing depressions 6 with, for example, a conventional heat-sealing die, thereby forming separate compartments for each reagent. The seals along areas 4 are purposely made breakable by carefully controlling the heat input or by forming only a narrow seal. Specifically, the formation of the seals can be controlled to provide seals capable of being later ruptured by the application of pressure to the reagents in the compartments. Alternatively, adhesives or other forms of bonding can be used, provided that rupturable bonds are formed in these areas. Heat and pressure are then applied to the three areas 3 to provide permanent, fluid-tight bonding at the three corresponding edges of sheets 7 and 8.

An elongate gas diffusion device 1 having a plurality of through-and-through channels 2 is positioned parallel and proximate to the fourth, unbonded edge of base sheet 7 and parallel and flush with the fourth, unbonded edge of top sheet 8. The open channels 2 of diffusion device 1 are thus oriented horizontally with respect to the plane of sheet 7 and perpendicularly with respect to the fourth edges of sheets 7 and 8. The diffusion device 1, thus sandwiched between sheets 7 and 8, is bonded to said sheets by the application of heat and pressure or by use of adhesives which should be impermeable and chemically inert to the collecting medium and reagents.

The bond between diffusion device 1 and each of sheets 7 and 8 should be liquid-tight and air-tight, thus completing the formation of reaction chamber 5, this chamber being the interior of the sealed receptacle formed between sheets 7 and 8 and containing the collecting medium. The relative positions of diffusion device 1 and sheets 7 and 8 are such that channels 2 provide the only communication between the atmosphere and the interior of reaction chamber 5.

It is also possible to form the dosimeter of FIGS. 2 and 3 saving the placement of the reagents and collecting medium, when these are liquids, for last. In such a case, the dosimeter is otherwise formed as described above. The reagents and collecting medium can be placed by piercing top sheet 8 at an appropriate spot with a hypodermic needle and injecting a measured amount of the collecting medium or reagent into the appropriate chamber or compartment. The holes made by the hypodermic needle can then be thermally sealed.

Diffusion device 1 allows the gaseous contaminant to diffuse through each of channels 2 according to Fick's Law, which is expressed in relevant form as $$M = D \cdot C \cdot tA/L$$

where

M = quantity of gaseous contaminant transferred (mg)

D = diffusion coefficient of the gaseous contaminant through air ($cm^2$/min)

C = concentration of the contaminant in the atmosphere (mg/$cm^3$)

t = time of exposure (minutes)

A = cross-sectional area of the channel ($cm^2$)

L = distance in direction of diffusion, herein channel length (cm)

Values of D for various gaseous contaminants are readily available from the literature. The purely diffusional nature of the transfer of the gaseous contaminant through the channels, at a rate in linear proportion to its atmospheric concentration, provides the integrating character of the dosimeter.

Gas diffusion device 1 is preferably made from materials that are non-hygroscopic and both chemically and physically inert to the gaseous contaminant and to the collecting medium. Examples are polyethylene, polypropylene, polymers or copolymers of tetrafluoroethylene and hexafluoropropylene, and stainless steel. The above-named polymers are preferred since they can be easily injection-molded.

As can be seen from Fick's Law, the number and diameter of the channels affect the quantity of gaseous contaminant collected since they affect the total cross-sectional area available for transfer. The quantity of contaminant collected is also inversely proportional to the length of the channels. Although these parameters are not necessarily critical to the integrating operation of the diffusion device, it has been found that the use of about 5-500 channels, preferably 10-100 channels each having a diameter of about 50-1000 microns and a length of about 1.0-25.0 mm, preferably 3.0-8.0 mm, provides a device that is sufficiently sensitive to low ambient contaminant concentrations but is still of a conveniently small size.

Optionally, a porous, hydrophobic film of 15-1000 micron thickness can be placed over the channel openings on the interior side 11 of diffusion device 1, the side communicating with the interior of reaction chamber 5. The film can be made, for example, of polymers or copolymers of tetrafluoroethylene and hexafluoropropylene. The function of the film is to prevent the absorbing solution, if that form of collecting medium is used, from flowing into the channels of diffusion device 1. Accordingly, the porosity of the film and the size of its pores should be selected so that this function is performed without interfering with the passage of the gaseous contaminant from the interior ends of the channels to the absorbing solution. That is, the diffusion of gaseous contaminant through this film should be significantly greater than the diffusion through the channels so that the overall rate of diffusion is essentially controlled only by the channels. It has been found that a film that is 50-80% porous with a pore size of 0.1-3.0 microns is sufficient for this purpose when channels as previously-described are used.

Other gas diffusion devices that can be used in the dosimeter of this invention are gas-permeable, liquid-impermeable membranes through which the gaseous contaminant can diffuse. Any of the conventionally known membranes are suitable for use herein with the proviso that the membrane be selected such that the rate of diffusion of the gaseous contaminant therethrough varies linearly with the atmospheric concentration of the contaminant through a broad range of such concentrations. This insures that a dosimeter using such membrane will integrate effectively. Where, for example, a membrane passes a quantity of gas at high atmospheric concentrations that is disproportionate to the amount passed at lower concentrations, the correlation between the final quantity collected and the average concentration in the atmosphere is destroyed. The membranes are normally about 10–300 microns in thickness and can be made, for example, of silicone rubber, polytetrafluoroethylene, or copolymers of silicone and polycarbamate.

Figure 4:
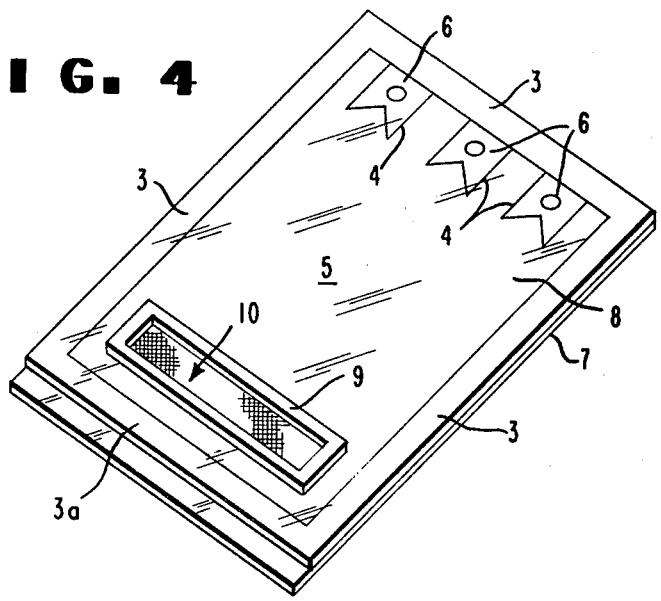
FIG. 4 is a perspective view of a gaseous contaminant dosimeter utilizing a membrane as the gas diffusion device.

A dosimeter of the present invention in which such a membrane is used as the gas diffusion device is shown in FIG. 4. The construction and description of this dosimeter are basically the same as was described with respect to the dosimeter of FIGS. 2 and 3 but with the following changes. In addition to sheets 7 and 8 being sealed along areas 3 as in FIGS. 2 and 3, sheets 7 and 8 of this dosimeter are also sealed in a similar manner on the fourth side 3a, completing the formation of reaction chamber 5.

Top sheet 8, forming a boundary of reaction chamber 5, is provided with a rectangular opening that is overlaid by a correspondingly-shaped membrane 10 of the kind previously described. A fastener 9, having the shape of the outline of a rectangle, overlays membrane 10 such that the rectangularly-shaped opening through fastener 9 exposes membrane 10 to the atmosphere. Fastener 9 is of the same material as sheet 8 and can be bonded thereto in a fluid-tight manner by the application of heat and pressure. Membrane 10 is thus sealed into top sheet 8 and provides the only communication between the atmosphere and the interior of reaction chamber 5.

In addition to the gas diffusion devices described herein, other devices usable in the present dosimeter are any of those that allow diffusion, or permeation, of the gaseous contaminant therethrough at a rate that varies linearly with the atmospheric concentration of the contaminant. For example, hollow fibers of the kind described in co-pending application Ser. No. 922,546 filed July 7, 1978 can be used.

Except for the inclusion of a diffusion device, the receptacle of the present dosimeter is substantially similar to the test pack shown in U.S. Pat. No. 3,476,515 issued Nov. 4, 1969. The disclosure of this patent is incorporated by reference herein.

In use, the dosimeter is exposed to the air containing the gaseous contaminant for a period of time for which the average contaminant concentration is sought. After exposure, the selected reagent compartments, containing the reagents necessary for analysis, are broken, their contents being released into the reaction chamber and mixed with the collecting medium therein. Breaking of the compartment is most easily accomplished by the application of pressure thereto, for example, by finger squeezing. The reagents and collecting medium can be thoroughly mixed by application of a light, pulsing force by the fingers on the pliable sheets forming the reaction chamber.

Since the dosimeter is pliable and transparent, the contents of the reaction chamber can be analyzed directly without withdrawing a sample from the dosimeter. For analysis to be made photometrically, the dosimeter can be clamped in a position where electromagnetic radiation can be directed through the contents of the reaction chamber with the unabsorbed (i.e., transmitted) radiation being directed to an appropriate detector. The preferred method is to use reagents which change the color of the collecting medium, depending on the amount of gaseous contaminant collected, and then analyzing with radiation in the range of visible light using a colorimeter or spectrophotometer.

The dosimeter of this invention can be calibrated to give a direct relationship between colorimetric or spectrophotometric readings and average ambient concentration of the gaseous contaminant. This can be accomplished by following a calibration procedure similar to that described in co-pending application Ser. No. 922,546, filed July 7, 1978. In such a procedure, several dosimeters are exposed over a given period of time to various known concentrations of a contaminant for which calibration is sought. The dosimeters contain the same kinds and amounts of collecting medium and reagents. Spectrophotometric readings, for example, are determined for at least two dosimeters at each of several known concentrations, and a straight-line is plotted, using a least-squares analysis, through the data points thus obtained.

What is claimed is:

1. A personal dosimeter for measuring the average concentration of a gaseous contaminant over a given period of time comprising:
   a pouch-like receptacle of polymeric material having at least one compartment, the compartment occupying less than the total volume of the receptacle, leaving a reaction chamber, the compartment containing a pre-determined quantity of a color-forming reagent and being adapted to release the reagent into the reaction chamber independently of any other reagents present in any other compartments, and the reaction chamber containing a collecting medium for the gaseous contaminant; and
   a gas diffusion device which is sealed into a boundary of the receptacle and through which the contaminant diffuses at a rate in linear proportion to its concentration in the atmosphere, the diffusion device providing the only communication between the atmosphere and the interior of the reaction chamber.

2. The dosimeter of claim 1 in which the gas diffusion device contains a plurality of through-and-through channels by which said communication is provided.

3. The dosimeter of claim 2 in which there are 5–500 channels, each having a diameter of 50–1000 microns and a length of 1.0–25.0 mm.

4. The dosimeter of claim 1 in which the gas diffusion device is a membrane through which the gaseous contaminant passes at a rate in linear proportion to its concentration in the atmosphere.

5. The dosimeter of claim 4 in which the membrane is constructed of silicone rubber, polytetrafluoroethylene, or copolymers of silicone and polycarbonate.

6. The dosimeter of claim 1, 2, 3, 4, or 5 wherein the collecting medium is in the form of an absorbing solution.

7. The dosimeter of claim 6 wherein the absorbing solution is for sulfur dioxide, nitrogen dioxide, or ammonia.

8. The dosimeter of claim 7 further containing at least one color-forming reagent.

9. The dosimeter of claim 8 wherein the absorbing solution is a solution of sodium tetrachloromercurate or potassium tetrachloromercurate in water and the reagent is for determining the presence of sulfur dioxide.

10. The dosimeter of claim 8 wherein the absorbing solution is a solution of triethanol amine in water and the reagent is for determining the presence of nitrogen dioxide.

11. The dosimeter of claim 8 wherein the absorbing solution is a solution of sulfuric acid in water and the reagent is for determining the presence of ammonia.

* * * * *